(12) United States Patent
Hurley et al.

(10) Patent No.: US 11,147,538 B2
(45) Date of Patent: Oct. 19, 2021

(54) EFFICIENT COMPUTATION OF SPATIALLY VARYING ULTRASOUND ANALYTICAL POINT SPREAD FUNCTIONS

(71) Applicant: INTERNATIONAL BUSINESS MACHINES CORPORATION, Armonk, NY (US)

(72) Inventors: Paul T. Hurley, Oberrieden (CH); Sepand Kashani, Rueschlikon (CH); Lucien Roquette, Rueschlikon (CH); Matthieu Simeoni, Lausanne (CH)

(73) Assignee: International Business Machines Corporation, Armonk, NY (US)

( * ) Notice: Subject to any disclaimer, the term of this patent is extended or adjusted under 35 U.S.C. 154(b) by 415 days.

(21) Appl. No.: 15/871,384

(22) Filed: Jan. 15, 2018

(65) Prior Publication Data

US 2019/0216432 A1 Jul. 18, 2019

(51) Int. Cl.
*A61B 8/08* (2006.01)
*G01S 15/89* (2006.01)
(Continued)

(52) U.S. Cl.
CPC ........ *A61B 8/5207* (2013.01); *A61B 5/02007* (2013.01); *G01S 7/52036* (2013.01);
(Continued)

(58) Field of Classification Search
CPC . A61B 8/5207; A61B 5/02007; A61B 8/4483; G01S 7/52036; G01S 15/8977;
(Continued)

(56) References Cited

U.S. PATENT DOCUMENTS 5,339,282 A * 8/1994 Kuhn .................... G01S 7/5205
367/7
7,063,666 B2 6/2006 Weng et al.
(Continued)

OTHER PUBLICATIONS

Rangarajan et al., "Ultrasonic Imaging Using a Computed Point Spread Function," IEEE Transactions on Ultrasonics, Ferroelectrics, and Frequency Control, Feb. 2008, p. 451-464, vol. 55, No. 2. (Year: 2008).*

(Continued)

*Primary Examiner* — Christopher Koharski
*Assistant Examiner* — Kaitlyn E Selmer
(74) *Attorney, Agent, or Firm* — Rakesh Roy

(57) ABSTRACT

A method for computing a tissue reflectivity function (TRF) is provided. This method comprises accessing radio-frequency (RF) data and computing a point spread function (PSF), to obtain the TRF. The RF data accessed are data obtained by beamforming time signals from an array of transducers of an ultrasound device. Next, for each pair (r, s) of given pairs of points in the imaging plane, the PSF is computed as a sum of contributions from at least some of the transducers. Each contribution is computed by evaluating a transducer's transfer function, based on two outputs of a respective time-of-flight function. Such outputs are obtained by evaluating the time-of-flight function at a first point r and at a second point s of each pair, respectively. Finally, the RF function can be deconvoluted, based on the computed PSF, so as to obtain the TRF.

14 Claims, 9 Drawing Sheets

(51) Int. Cl.
G01S 7/52 (2006.01)
A61B 5/02 (2006.01)
A61B 8/00 (2006.01)

(52) U.S. Cl.
CPC ......... *G01S 15/8977* (2013.01); *A61B 8/4483* (2013.01); *G01S 7/52085* (2013.01)

(58) Field of Classification Search
CPC ............. G01S 7/52047; G01S 7/52077; G01S 15/8915; G01S 7/52028; G06T 5/003; G06T 5/00; G02B 7/36
See application file for complete search history.

(56) References Cited

U.S. PATENT DOCUMENTS

| | | | |
|---|---|---|---|
| 8,652,045 | B2 | 2/2014 | Waters et al. |
| 9,058,656 | B2 * | 6/2015 | Benameur ............... G06T 5/003 |
| 9,117,439 | B2 * | 8/2015 | Bercoff ............... G10K 11/346 |
| 9,247,926 | B2 | 2/2016 | Smith et al. |
| 9,295,444 | B2 | 3/2016 | Schwartz et al. |
| 9,538,987 | B2 * | 1/2017 | Hoctor ................. A61B 8/4477 |
| 2004/0054281 | A1 * | 3/2004 | Adam ................. G01S 7/52077 600/437 |
| 2006/0078196 | A1 | 4/2006 | Sumanaweera et al. |
| 2008/0289423 | A1 * | 11/2008 | Gordon ..................... G06T 7/10 73/602 |
| 2016/0128675 | A1 * | 5/2016 | Kang ................... A61B 8/5246 600/443 |
| 2017/0003384 | A1 | 1/2017 | Christiansen et al. |
| 2017/0184713 | A1 * | 6/2017 | Robert ............... G01S 15/8927 |

OTHER PUBLICATIONS

Dalitz et al., "Point Spread Functions and Deconvolution of Ultrasonic Images," IEEE Transactions on Ultrasonics, Ferroelectrics, and Frequency Control, Mar. 2015, p. 531-544, vol. 62, No. 3. (Year: 2015).*

Ahmad et al., "Coarray Analysis of the Wide-Band Point Spread Function for Active Array Imaging," Signal Processing, Jan. 2001, p. 1-4, vol. 81, Issue 1, Elsevier Science B.V., Abstract Only, http://www.sciencedirect.com/science/article/pii/S0165168400001936#aep-abstract-id14, Accessed on Oct. 16, 2017.

Alessandrini et al., "A Restoration Framework for Ultrasonic Tissue Characterization," IEEE Transactions on Ultrasonics, Ferroelectrics, and Frequency Control, Nov. 2011, p. 2344-2360, vol. 58, No. 11.

Chen et al., "Beamforming-Deconvolution: A Novel Concept of Deconvolution for Ultrasound Imaging," International BASP Frontiers Workshop, Jan. 29-Feb. 3, 2017, 1 Page, EPFL-CONF-223426, Villars sur Ollon, Switzerland.

Chen et al., "Compressive Deconvolution in Medical Ultrasound Imaging," IEEE Transactions on Medical Imaging, Mar. 2016, p. 728-737, vol. 35, No. 3.

Dalitz et al., "Point Spread Functions and Deconvolution of Ultrasonic Images," IEEE Transactions on Ultrasonics, Ferroelectrics, and Frequency Control, Mar. 2015, p. 531-544, vol. 62, No. 3.

David et al., "Time Domain Compressive Beam Forming of Ultrasound Signals," The Journal of the Acoustical Society of America, May 2015, p. 2773-2784, vol. 137, Issue 5.

Jensen et al., "Calculation of Pressure Fields from Arbitrarily Shaped, Apodized, and Excited Ultrasound Transducers," IEEE Transactions on Ultrasonics, Ferroelectrics, and Frequency Control, Mar. 1992, p. 262-267, vol. 39, No. 2.

Jensen et al., "Deconvolution of In-Vivo Ultrasound B-Mode Images," Ultrasonic Imaging, 1993, p. 1-16, vol. 15, No. 2.

Mattausch et al., "Image-Based PSF Estimation for Ultrasound Training Simulation," Simulation and Synthesis in Medical Imaging (SASHIMI 2016), 2016, p. 23-33, LNCS 9968, Springer International Publishing AG.

Michailovich et al., "Adaptive Learning of Tissue Reflectivity Statistics and Its Application to Deconvolution of Medical Ultrasound Scans," IEEE International Ultrasonics Symposium Proceedings, 2015, 4 Pages.

Michailovich, "Non-Stationary Blind Deconvolution of Medical Ultrasound Scans," Procedings of SPIE Medical Imaging 2017: Ultrasonic Imaging and Tomography, 2017, p. 1-11, vol. 10139, Orlando, Florida.

Michailovich et al., "A Novel Approach to the 2-D Blind Deconvolution Problem in Medical Ultrasound," IEEE Transactions on Medical Imaging, Jan. 2005, p. 86-104, vol. 24, No. 1.

Rangarajan et al., "Ultrasonic Imaging Using a Computed Point Spread Function," IEEE Transactions on Ultrasonics, Ferroelectrics, and Frequency Control, Feb. 2008, p. 451-464, vol. 55, No. 2.

Roquette et al., "On an Analytical, Spatially-Varying, Point-Spread-Function," 2017 IEEE International Ultrasonics Symposium (IUS), Sep. 6-9, 2017, 4 Pages, Grace Period Disclosure.

Wygant et al., "Integrated Ultrasound Imaging Systems Based on Capacitive Micromachined Ultrasonic Transducer Arrays," IEEE Sensors, 2005, p. 704-707.

* cited by examiner

EFFICIENT COMPUTATION OF SPATIALLY VARYING ULTRASOUND ANALYTICAL POINT SPREAD FUNCTIONS

STATEMENT REGARDING PRIOR DISCLOSURES BY THE INVENTOR OR A JOINT INVENTOR

Aspects of the present invention have been disclosed by the inventors in the paper "On an Analytical, Spatially-Varying, Point-Spread-Function," published in the Proceedings of the 2017 IEEE International Ultrasonics Symposium (IUS), made available to the public on Sep. 6-9, 2017. The following disclosure is submitted under 35 U.S.C. § 102(b)(1)(A).

BACKGROUND

The invention relates in general to the field of computer-implemented methods for computing a spatially varying point spread function of an ultrasound apparatus from time signals obtained from transducers thereof, e.g., in order to subsequently compute tissue reflectivity functions, as well as to related ultrasound apparatuses.

Medical imaging is still a fast-developing research area, which is known to bring additional insights into diagnosis assistance. For instance, computed tomography methods exploiting X-ray and magnetic resonance imaging are known to provide high quality images of the body structure. However, such methods suffer from drawbacks, which notably include the cost of the acquisition system and a lack of portability. All the more, injection of active molecules in patient's body is required. Medical ultrasound may be regarded as a complementary imaging method, which is cheap, non-invasive, fast, and portable (to some extent). This makes ultrasound imaging an active research topic; efforts have been invested to overcome the main disadvantage of this technology, i.e., the low-contrasts obtained between the scanned body regions.

A usual medical ultrasound acquisition system comprises a probe, i.e., a linear-array of transducers, wired to a processing unit that computes and displays the scanned region. A transducer as used in such devices is typically a piezoelectric element converting electrical signals into a sound wave, and conversely, a sound wave into electrical signals. In medical applications, the probe usually generates waves within a frequency range of 1 to 20 MHz. The human body reflects such waves with an intensity that depends on the medium's reflectivity. The processing unit is configured to reconstruct intensity levels of the body's reflectivity based on time signals recorded at each transducer. High reflections usually arise when the waves pass through a density discontinuity of the internal body's surface. Now, the fact that the density structure lacks of regularity typically leads to loosely defined boundaries on the displayed image. Thus, post-processing methods are needed, to attempt to obtain sharper surface boundaries, e.g., in order to enable improved detection of tissue abnormalities such as tumors.

Some of the known methods to compute the tissue reflectivity function require an estimation of the so-called point spread function, or PSF, which function describes the response of the imaging system to a point source. In general, the estimation of the ultrasound PSF either assumes that the function is spatially invariant (i.e., it can be described by a spatially-invariant filter) or resorts to involved simulations, in order to calculate this function at various fixed points.

In more detail, the most common method for estimating the tissue reflectivity function (hereafter TRF) is the so-called Delay-And-Sum (DAS) method. This reconstruction technique can be regarded as a beamforming technique, whereby suitably delaying and summing the transducers signals allows to focus a signal coming from a particular point in space. Yet, in ultrasound imaging, the beamforming technique does actually not provide an estimate of the TRF. Rather, it leads to the so-called radio-frequency (RF) image, which can be thought of as a "blurred" version of the TRF image. RF images do not account for the device's physical limitation, which is instead characterized by the PSF of the device. The RF image can be conceptualized as a convolution between the PSF and the unknown TRF.

Post-processing techniques for image enhancement tackle the deconvolution problem, i.e., they attempt to reduce the effect of limited devices capabilities. The deconvolution problem can be mathematically expressed as the minimization of an objective function, whereby the distance between an estimated RF image and the PSF convolved with the unknown TRF need be minimized. This optimization problem is commonly subject to regularization. This brings prior information on the TRF structure, improving the ill-posedness or conditioning of the deconvolution problem. For instance, one may impose a penalization in the $l_p$-norm on the TRF ensuring inversion stability. This procedure is equivalent to inject prior knowledge on the TRF structure. For example, the $l_1$ norm can be used to promote sparsity.

There are essentially two main active research directions in the field of deconvolution for ultrasound. The first axis focuses on the choice of the prior information to use with respect to tissue characterization. The second axis is concerned with the computation of the system's PSF, for which no closed-form formula exist. Thus, the PSF need, in general, be crudely approximated. Prior methods to obtain the PSF may be summarized as follows:

Simulation methods: the software "Field II" generates simulated ultrasound data. It is widely used and accepted in the community. For every fixed point in an empty medium and a particular probe/acquisition system, a new simulation must be run to obtain the PSF associated with this point, which is computationally intractable in practice. To circumvent this problem, it is normally assumed that the PSF is spatially invariant. However, such an approximation is particularly crude and limits the achievable quality enhancement. A similar approach can be conducted with a real acquisition system. However, it suffers from the same drawbacks.

Estimation methods: The PSF may be estimated from the data along with the deconvolution, which method is commonly referred to as blind deconvolution. Several methods exist, which allow this to be achieved, but they are rather computationally intensive. Machine learning approaches have further been developed to learn the PSF from experimental images. However, such methods involve complex optimization problems. Basically, a spatially invariant PSF must be assumed.

PSF computation methods: analytical and numerical approximations to the PSF have been explored. Yet, only the numerical approximations to the PSF account for its spatially varying behavior in the near-field. Besides, such numerical approximations have not been extended to linear arrays of transducers.

SUMMARY

According to a first aspect, the present invention is embodied as a computer-implemented method for computing a tissue reflectivity function, or TRF. This method basically comprises accessing radio-frequency data, or RF data, and computing a point spread function, or PSF, to obtain the TRF. The RF data accessed are data obtained by beamforming time signals $R_i$ from an array of transducers of an ultrasound device. The RF data are assumed to correspond to outputs of a radio-frequency function, or RF function, as evaluated at given points r of an imaging plane. The RF function is assumed to involve a convolution of the PSF with the TRF to be computed, where the PSF is here assumed to be defined at pairs of points of the imaging plane, so as to account for a spatial variance thereof.

Next, for each pair (r, s) of given pairs of points in the imaging plane, the PSF is computed as a sum of contributions from at least some of the transducers, to which respective time-of-flight functions can be associated. Each of said contributions is computed by evaluating a transducer's transfer function h, based on two outputs of the respective time-of-flight function $\tau$. Such outputs are obtained by evaluating the time-of-flight function at a first point r and at a second point s of said each pair, respectively. Finally, the RF function can be deconvoluted, based on the computed PSF, so as to obtain the TRF.

The above method allows the PSF of an ultrasound apparatus to be efficiently computed, even though the PSF is defined so as to account for a spatial variance thereof. The underlying scheme relies on an analytical approximation to the PSF, which requires no simulation, such that a spatially varying PSF can easily be computed.

This in turn allows more efficient post-processing techniques, leading to sharper images with higher resolution and contrasts. In that respect, the present methods shall, preferably, further comprise displaying an image based on the computed TRF. In general, the present approach can be applied to ultrasound imaging techniques and related deconvolution methods. It can further be applied for probe setup purposes.

In embodiments, when computing the PSF, each of said contributions is computed by evaluating the transducer's transfer function h as a function of a difference between the two outputs of the time-of-flight function $\tau$. The PSF may for instance be computed as a sum that can be written as $\Sigma_i h(\tau(r, p_i) - \tau(s, p_i)) \times b_i$, where $p_i$ denotes a position in space of an $i^{th}$ transducer of the array, i=1, . . . N, and $b_i$, is a correction factor, which may possibly be assumed to be equal to 1. Introducing such a correction factor allows additional effects to be taken into account.

Preferably, the method further comprises accessing an explicit representation of the RF function that is constructed based on time signals $R_i$ obtained from the transducers of said array. The TRF is subsequently obtained by deconvoluting the constructed RF function, based on the accessed representation of the RF function. This explicit representation of the RF function may for instance be obtained by interpolating the time signals $R_i$ from the transducers.

The computation of the PSF may advantageously involve an interpolation of the transfer function h, which is based on a same interpolation scheme as used to interpolate the time signals $R_i$ to construct the RF function. This way, the PSF is evaluated consistently with the RF function, such that no additional bias is introduced in the computation of the PSF.

To that aim, a representation of the transducer's transfer function h as an analytical function may need be accessed. More generally though, embodiments of the present methods may rely on an analytical representation of h, for its evaluation, without necessarily involving an interpolation thereof. The analytical function accessed can typically be written as a decaying function times an oscillating function. For example, it may be written as $h(t)=\beta e^{-\alpha t^2} \cos(2\pi f_0 t)$, where $\beta$ is a constant.

Preferably, the array of transducers is configured to cause, in emission, a plane wave corresponding to a coherent summation of circular waves emitted by each of the transducers. In that case, the time-of-flight function r associated with an $i^{th}$ transducer of the array can be computed, for a given point r, as $\tau(r, p_i) = (r, e_y)/c + \|r - p_i\|/c$, where c is the speed of sound in the target medium, whose TRF is to be computed, and $p_i$ corresponds to a position of the $i^{th}$ transducer. The plane wave is assumed to be directed in the direction of the unit vector $e_y$.

In other cases, the array of transducers may be configured to cause a coherent divergent wave in emission. Assuming this wave has a virtual point source $r_n = (x_n, y_n)$, the time-of-flight function $\tau$ associated with the $i^{th}$ transducer of the array can now be computed, for a given point r, based on the relation $\tau(r, p_i) = (\|r - r_n\| - (r_n, r)/c + \|r - p_i\|/c$, where c is the speed of sound in the target medium and $p_i$ corresponds to the position of the $i^{th}$ transducer.

According to another aspect, the invention is embodied as an ultrasound apparatus. Basically, this apparatus comprises an array of transducers and a processing module.

The transducers are, each, configured to convert an electrical signal into a sound wave, in order to emit such a sound wave and, conversely, to convert a sound wave it receives into an electrical signal. Time signals can be obtained from the array of transducers, in operation, based on which the RF image can be computed in practice.

The processing module comprises: a beamforming module; a PSF module; and a deconvolution module. The beamforming module is configured to beamform time signals obtained from the array of transducers, so as to obtain RF data. Again, the RF data are assumed to correspond to outputs of a RF function, which involves a convolution of the PSF with the TRF, and the PSF is assumed to be defined at pairs of points in the imaging plane, so as to account for a spatial variance thereof.

The PSF module is configured to access RF data as obtained via the beamforming module. Consistently with the present methods, this module is further configured to compute the PSF for each pair (r, s) of points of interest, as a sum of contributions from at least some of the transducers, to which time-of-flight functions can respectively be associated. In operation, the PSF module computes each of said contributions by evaluating a transducer's transfer function h, based on outputs of the respective time-of-flight function $\tau$, evaluated in r and s.

Finally, the deconvolution module is configured to deconvolve the RF function associated to RF data as accessed by the PSF module, to obtain the TRF, based on a PSF as computed by the PSF module, in operation.

Preferably, the processing module further comprises an interpolation module, which is configured in the processing module so as to be invoked by the beamforming module. The interpolation module is otherwise configured to interpolate time signals $R_i$ obtained from the array of transducers, so as to provide interpolated time signals to the beamforming module, for the latter to construct the RF function, in operation.

In preferred embodiments, the interpolation module is further configured so as to be further invoked by the PSF module. This way, the interpolation module may interpolate the transfer function h, so as to provide to the PSF module a transfer function h interpolated based on a same interpolation scheme as used to interpolate the time signals to obtain the RF function, in operation.

According to another aspect, the invention is embodied as a computer program product for computing a tissue reflectivity function (TRF). The computer program product comprises a computer readable storage medium having program instructions embodied therewith, where the program instructions are executable by a processing unit to cause the latter to take steps according to embodiments of the present methods, i.e., to access RF data, compute the PSF, and deconvolve the RF function to obtain the TRF.

Devices, methods and computer program products embodying the present invention will now be described, by way of non-limiting examples, and in reference to the accompanying drawings.

BRIEF DESCRIPTION OF SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description.

FIG. 4A depicts a time domain representation of h(t), whereas FIG. 4B shows a corresponding frequency domain representation.

FIG. 6A is obtained using known simulation methods, whereas FIG. 6B is obtained thanks to embodiments of this invention.

The accompanying drawings show simplified representations of devices or parts thereof, as involved in embodiments. Similar or functionally similar elements in the figures have been allocated the same numeral references, unless otherwise indicated.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The following description is structured as follows. First, general embodiments and high-level variants are described (sect. 1). The next section addresses more specific embodiments and technical implementation details (sect. 2 and 3).

1. General Embodiments and High-Level Variants

Figure 1:
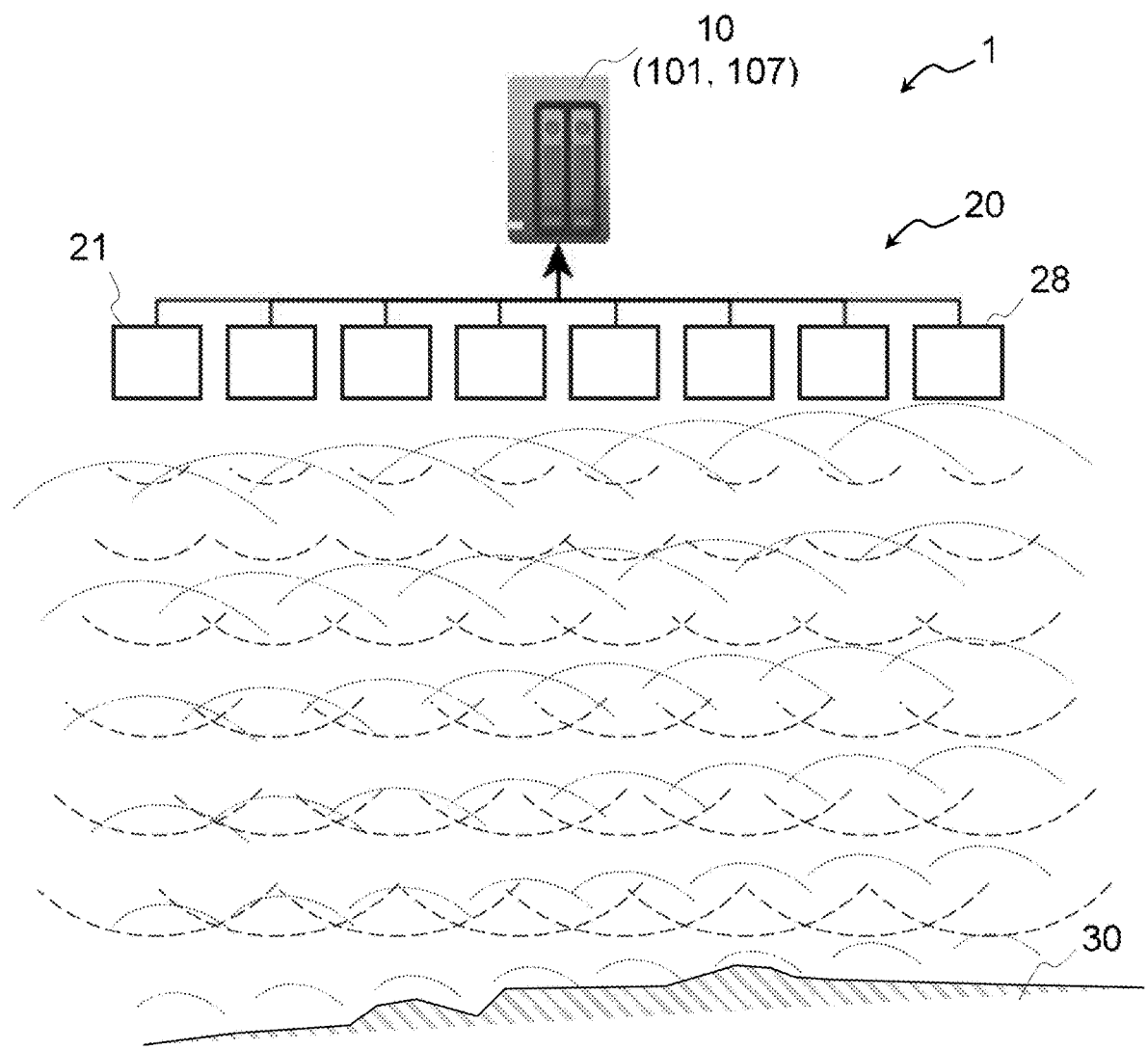
FIG. 1 schematically illustrates the operation of an ultrasound device, according to embodiments.
Figure 2:
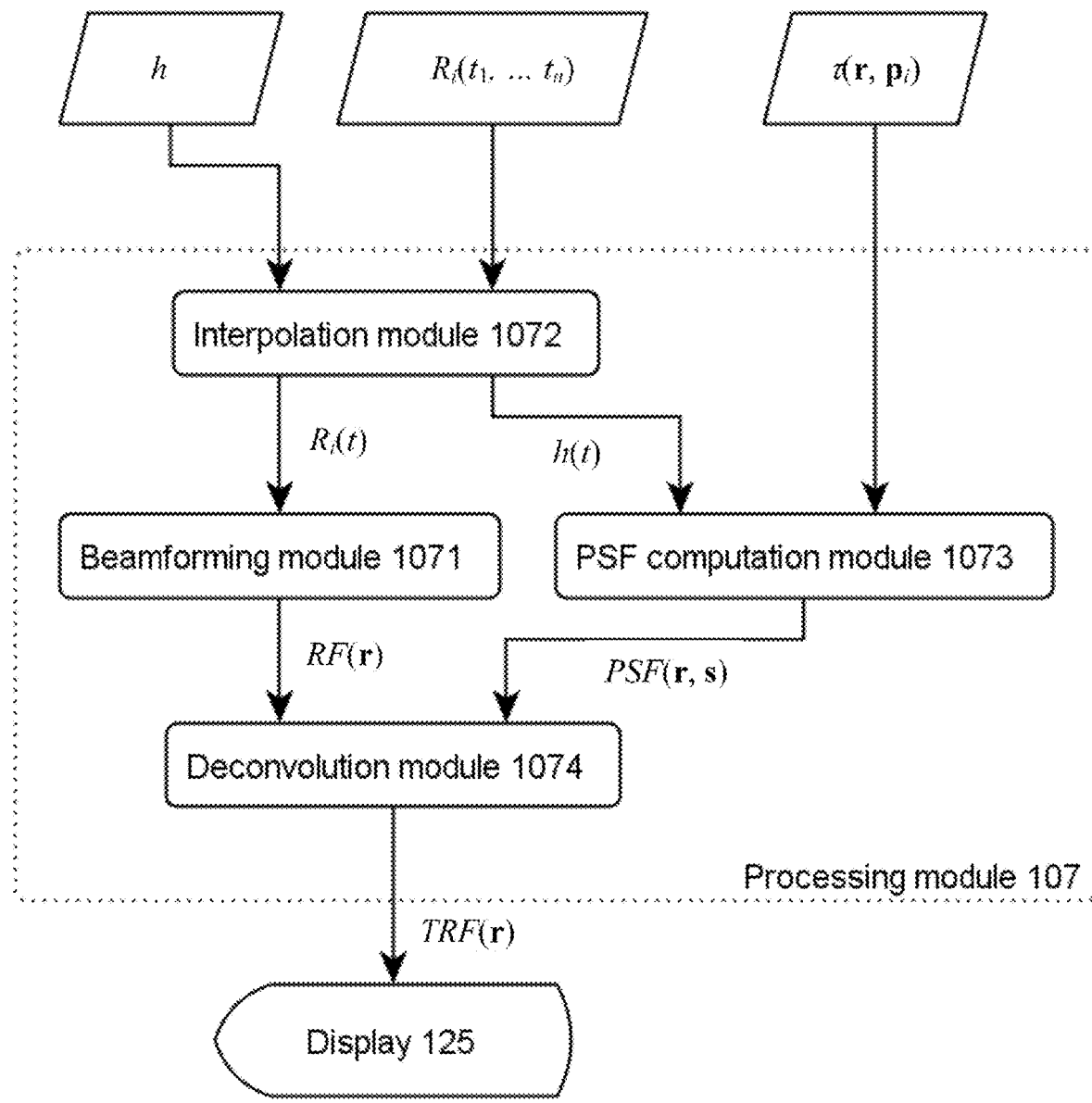
FIG. 2 is a block diagram that schematically depicts selected components of a processing module of an ultrasound device and how such components interact to compute a point spread function and a tissue reflectivity function, as involved in embodiments.
Figure 3:
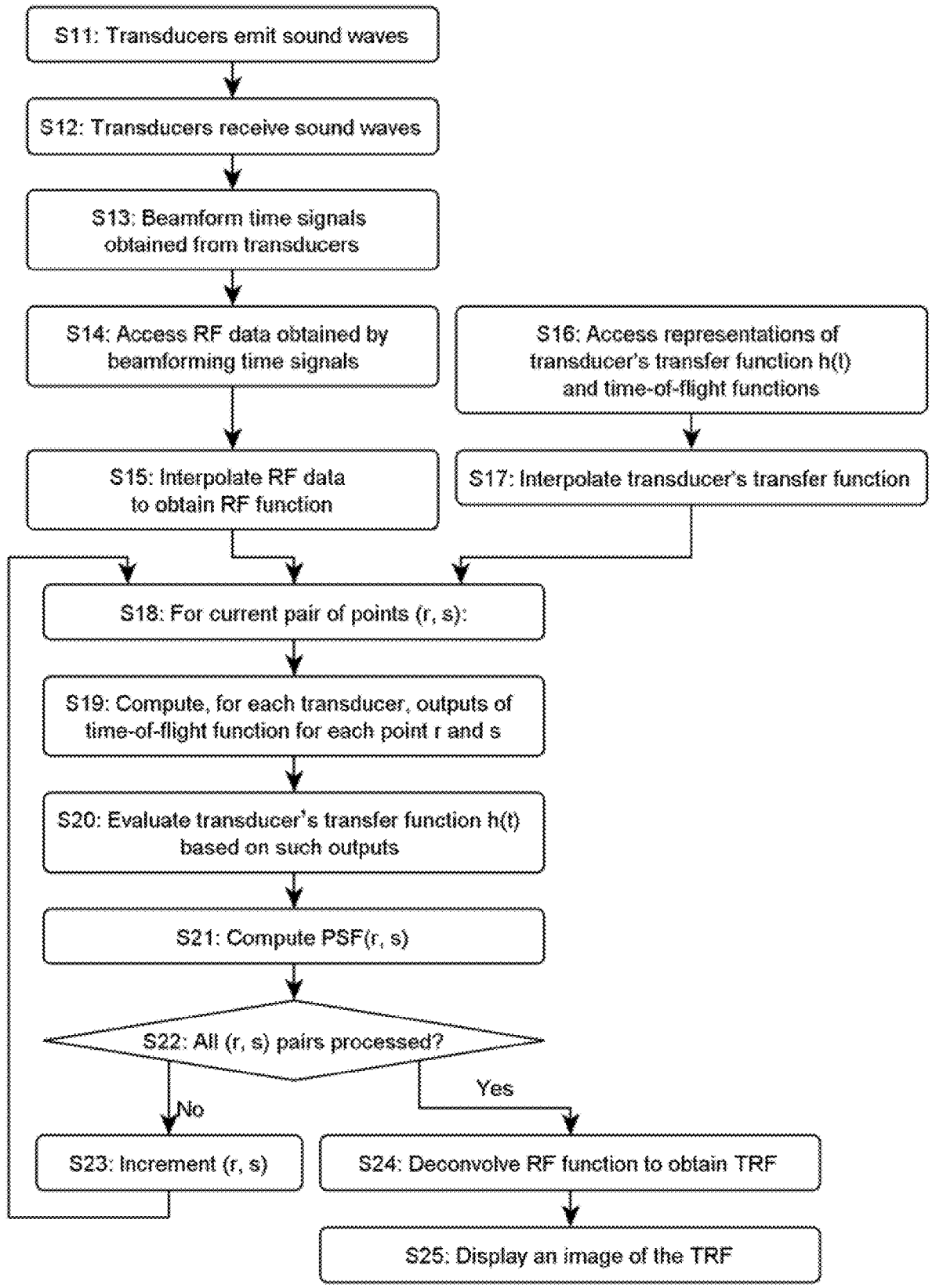
FIG. 3 is a flowchart illustrating high-level steps of a method for computing such a tissue reflectivity function, according to embodiments.

In reference to FIGS. 1-3, an aspect of the invention is first described, which concerns computer-implemented methods for computing a tissue reflectivity function, or TRF. As reflected in FIGS. 2 and 3, such methods involves three stages, where: (i) radio-frequency data are obtained; (ii) the point spread function (PSF) is computed; and (iii) the TRF is obtained based on the PSF.

First, such methods rely on radio-frequency data, or RF data, accessed at step S14 (see the flowchart of FIG. 3). The accessed RF data are assumed to have been obtained (step S13) by beamforming time signals $R_i$ (i.e., time-series) collected S12 by an array 20 of transducers 21-28 of an ultrasound device 1 (see FIG. 1).

Beamforming, in this context, amount to delay and sum the transducers signals, which in turn makes it possible to focus on a particular point in space. In the context of ultrasound techniques, beamforming and delay-and-sum (DAS) techniques are synonymous. The aim of the DAS process is to be able to evaluate the RF function from the time signals $R_i(t_1, t_2, \ldots)$, i.e., the signals recorded by the $i^{th}$ transducer.

For the purpose of implementing the present methods, the RF data are assumed to correspond to outputs of a radio-frequency function (hereafter RF function), as evaluated at given points r of the imaging plane, i.e., the plane to which the RF data pertain and in which the TRF function may eventually be displayed. For reasons evoked earlier, this RF function can be devised as a convolution of the point spread function (PSF) with the TRF, i.e., the unknown function to be retrieved. Importantly, the PSF is here assumed to be defined at pairs of points of the imaging plane, so as to account for its spatial variance.

The PSF is estimated as follows. For each pair (r, s) of given pairs of points in the imaging plane, the PSF is computed S18-S22 as a sum of contributions from at least some of the transducers 21-28. Time-of-flight functions can be respectively associated to the transducers, as explained later in detail. Each of the contributions to the PSF is computed by evaluating S20 the transducer's transfer function h (also called pulse function), where the latter takes as argument two outputs of the time-of-flight function τ associated to each contribution (i.e., respectively associated to each transducer considered for the computation of the PSF), where the function t is evaluated at each of the points of each pair (r, s) considered.

In other words, the outputs of the time-of-flight function r are obtained S19 by evaluating the relevant time-of-flight function twice, a first time at point r and a second time at point s of the pair (r, s) and, this, for each of the contributions to be computed. I.e., each of said contributions involves two outputs of a respective time-of-flight function τ.

To fix ideas, the PSF may for instance be evaluated based on the equation:

$$PSF(r,s)=\Sigma_i h[\tau(r,p_i);\tau(s,p_i)], \quad (1)$$

where $p_i$ denotes a position in space of the $i^{th}$ transducer, $i=1, \ldots N$, and the sum is performed over each of the transducers taken into account. This amounts to sum outputs of the function h, which is a function of $\tau(r, p_i)$ and $\tau(s, p_i)$, i.e., the time-of-flight function associated to the $i^{th}$ transducer by way of its dependence on $p_i$, and respectively evaluated in r and s.

Note that the italic notation "PSF" is used to denote a (specific) mathematical object, as in Eq. 1 above, contrary to the non-italic notation "PSF", which is a short notation for a (general) point spread function. The same distinction is later made between "RF function" and "RF".

In the present approach, contributions from some or all of the transducers 21-28 may be involved and, this, for each pair (r, s) of points considered in the imaging plane. All pairs of points (e.g., as defined on a grid, for a given resolution) are normally considered. Yet, some particular points (or pairs of points) might be skipped, should some approximation or simplification (e.g., symmetry) assumption be available. Also, instead of considering pairs of points, the PSF may for instance equivalently be computed based on intracular and extracular space coordinates R and σ, where R=r+s/2 and σ=r−s. More generally, any rotation of the coordinates (r, s) may be contemplated, e.g., r, r+s, etc. In addition, other coordinate systems might be considered. Yet, in all cases, the PSF as considered herein fundamentally remains a two-point function, which makes it possible to capture the spatial variability of the PSF.

That the PSF is spatially varying means that $PSF(r_1, r_2) \neq PSF(r_1-(r_2-r_3), r_3)$, whereas a spatially invariant PSF fulfills the condition $PSF_I(r_1, r_2)=PSF_I(r_1-(r_2-r_3), r_3)$, where $r_1$, $r_2$ and $r_3$ are 2D vectors pointing at points in the 2D imaging plane. The subscript I is used in the latter to distinguish the spatially invariant function $PSF_I$ from a spatially varying function PSF(.,.) as computed herein. This is discussed later in detail.

Normally, all contributions from each transducer will be taken into account. However, the PSF may possibly be estimated based on contributions from a subset of the transducers 21-28 only, if necessary. For example, some of the transducers may be discarded, on purpose, e.g., because their locations is expected to introduce a bias or some of the transducers are not fully functional, etc.

Finally, the RF function can be deconvoluted S24 based on the computed PSF, step S21, to obtain the TRF. Any suitable deconvolution scheme can be contemplated at this step. Examples are mentioned in sect. 2.

If all pairs were not processed at step S22, then, at step S23 the pair (r, s) may be incremented before returning to S18.

The present approach makes it possible to efficiently compute the PSF of the ultrasound device, even though the PSF is defined so as to account for a spatial variance thereof.

Yet, and as present Inventors have realized, the PSF can be computed as a sum of contributions, each involving the transducer's transfer function h, suitably delayed thanks to outputs of the time-of-flight function τ. Exploiting this possibility, the present approach leverages an analytical approximation to the spatially varying PSF, such that the PSF can, eventually, easily be computed, without resorting to involved simulations or numerical approximations.

This, in turn, allow more efficient post-processing techniques, leading to sharper images with higher resolution and contrasts. I.e., the present methods are typically used to display S25 an image of the target medium 30 (FIG. 1) or internal surfaces thereof, based on the computed TRF, as they are particularly suited for real-time processing. In general, the present approach can be applied to ultrasound imaging techniques and related deconvolution methods. It may further be applied for probe setup purposes.

Preferred embodiments are now described. To start with, when computing the spatially varying PSF, each contribution from each transducer is preferably computed by evaluating S20 the transducer's transfer function h as a function of a difference between said two outputs. I.e., the PSF may for example be evaluated as:

$$PSF(r,s)=\Sigma_i h[\xi(r,p_i)-\tau(s,p_i)]. \quad (2)$$

However, in variants, outputs from the time-of-flight functions may be provided in the form of ratios $\gamma(r, s, p_i)=\tau(r, p_i)/\tau(s, p_i)$ to the PSF computation algorithm, as per a design choice in the algorithm. In such cases, the transducer's transfer function may subsequently be evaluated as $h[\tau(s, p_i) \times (\gamma(r, s, p_i)-1)]$. Other variants may still lead to distinct implementations of the computation of h, such that, more generally, the PSF is said to be computed based on contributions involving, each, the transfer function h, which is evaluated based on distinct outputs $\tau(r, p_i)$ and $\tau(s, p_i)$ of the time-of-flight function. Still, the PSF may equivalently be computed in the Fourier space, making use of the convolution theorem.

In more sophisticated embodiments, the PSF may be computed S21 as a sum that can be written as $\Sigma_i h[\tau(r, p_i); \tau(s, p_i)] \times b_i$, where $b_i$ is a correction factor. Again, $p_i$ denotes the position in space of the $i^{th}$ transducer of the array 20, $i=1, \ldots N$. The correction factor $b_i$ may, in general, vary from one transducer to the other. It may further be non-constant, i.e., spatially varying. In the simplest cases, this correction factor is assumed to be equal to 1, as noted earlier. E.g., $$PSF(r,s)=\Sigma_i h[\tau(r, p_i);\tau(s,p_i)].$$

However, this factor may also be devised so as to take into account, e.g., an array pattern $(b_i=b(r)\forall_i)$, accounting for a spatial selectivity. That is, the correction factor b varies in space but is identical for all transducers in that case. As another example, the correction factor may capture a decay law, to account for attenuation.

In other variants, an apodization strategy may be contemplated, whereby signals obtained from the transducers may be re-weighted. I.e., a re-weighting method is applied on the transducer channels in that case, in order to compute the RF-image.

In addition, distinct transducer's transfer functions $h_i$ may be assumed for some of each of the transducers and, thus, for some or each of the contributions $h_i[\tau(r, p_i); \tau(s, p_i)] \times b_i$ to the PSF.

In preferred embodiments, the present methods rely on an explicit representation of the RF function, for deconvolution purposes. That is, an explicit representation of the RF function is accessed (after step S15 and before step S24 in FIG. 3), which function is constructed, steps S13-S15, based on time signals $R_i$ as obtained S12 from the transducers 21-28 of the array 20. Thus, the TRF can subsequently be obtained by deconvoluting S24 the constructed RF function, based on the accessed representation thereof. To that aim, an interpolation scheme may be used, as discussed below. An explicit expression for the RF function makes it possible to compute the constructed function for all points r of interest in the imaging plane. In variants, other approximation techniques might be involved, e.g., where inferred analytical expressions are fitted onto given datasets. In other variants, numerical methods might be used, without it being necessary to resort to an explicit representation of the RF function.

Preferably though, the RF function is constructed S13-S15 by interpolating S15 the time signals $R_i$ obtained S12 from the transducers 21-28. This way, an explicit representation of the RF function can easily be obtained.

In detail, the RF function can generally be written as $RF(r)=\Sigma_i R_i[\tau(r, p_i)]$, where $R_i(.)$ is the time-signal recorded by the $i^{th}$ transducer. Now, we note that the RF function cannot be directly computed from the time signals $R_i(t_1, t_2, \ldots)$ as obtained from the transducers since values of $R_i$ are only available for discrete time samples. Thus, an interpolation scheme may advantageously be introduced, in order to be able to more easily evaluate the $R_i$ function, at any desired delay $\tau(r, p_i)$. Yet, in variants, an analytical expression of $R_i$ may be devised and subsequently fitted onto the available datasets. However, an interpolation would likely be more accurate, while computationally not more intensive.

Interestingly, the computation of the PSF may further comprises interpolating S17 the transfer function h, based on the same interpolation scheme as used to interpolate S15 the time signals $R_i$ when constructing the RF function. That is, the computation of the PSF is preferably conducted using the same context as otherwise used to compute the RF function, so that the PSF is evaluated consistently with the evaluation of the RF function. This way, no extra bias is introduced in the deconvolution scheme.

That a same interpolation scheme be used means that a same interpolation technique is involved, which uses a same or a common strategy. For example, same interpolation time points as used to compute the time signals $R_i$ may be used and the functions h and $R_i$ may be constrained to exactly match such points. In addition, the same type of functions (e.g., polynomials, splines) are preferably considered to interpolate the time signals and the transfer function, and, e.g., a same polynomial order may be used in each case, etc.

In variant, the transfer function h(t) may be analytically formulated and thus computed for any input values, without any interpolation being needed therefor. However, best is to rely on a same approximation technique for the computation of the functions h and $R_i$, to avoid or mitigate additional biases. Be it interpolated or not, the transfer function h is preferably provided as an analytical function. I.e., the present methods may access S16 a representation of the transducer's transfer function h as an analytical function, prior to evaluating it at step S20. In variants, numerical approximations to h may be relied on, though such variants are believed to be less stable and computationally more intensive.

The analytical representation of h, as accessed at step S16, may for instance be simply written as a decaying function (e.g., any exponentially decaying function) times an oscillating function (e.g., polynomial or a trigonometric function), which would suffice to describe most cases of interest, as illustrated in sect. 2. For example, the analytical function h may be written as $h(t)=\beta e^{-\alpha t^2} \cos(2\pi f_0 t)$, where $\beta$ is a constant, which can typically be set equal to 1.

Different expression of the function $\tau(r, p_i)$ may be relied on, depending on the context at issue and the corresponding physics. For example, where the array 20 of transducers 21-28 is configured to generate a plane wave (in emission S11), i.e., a wave corresponding to a coherent summation of circular waves emitted by each of the transducers, then the time-of-flight function may be computed S19, for a given point r, as $\tau(r, p_i)=(r, e_y)/c+\|r-p_i\|/c$. Here, the plane wave is assumed to be directed in the direction of the unit vector $e_y$, c is the speed of sound in the target medium 30 (whose TRF is to be computed), and $p_i$ corresponds to the position of the $i^{th}$ transducer.

In variants where the transducers 21-28 are configured to generate S11 a coherent divergent wave, the function $\tau$ associated with the $i^{th}$ transducer would instead be computed S19, for a given point r, as $\tau(r, p_i)=(\|r-r_n\|-(r_n, r)/c+\|r-p_i\|/c$. The point $r_n=(x_n, y_n)$ corresponds to the virtual point source (also called focal point), which is a virtual emission point, i.e., the virtual origin of the diverging wave. This point is typically located behind the array of transducers, i.e., opposite to the medium 30 with respect to the array 20 of transducers. All this is illustrated in sect. 2.

Additional insights can be gained by examining the mathematical background for the present approach. Assume that the time-of-flight law $\tau(r, p)$, the transfer function h(t) and the probe geometry $p_1, \ldots, p_N$ are known. As mentioned earlier, the RF image computed by a standard delay-and-sum technique may be expressed (at a continuous level) by:

$$RF(r)=\Sigma_{i=1}^N R_i[\tau(r;p_i)], \quad (3)$$

where $R_i(\cdot)$ is the time-signal recorded by the $i^{th}$ transducer, for $t \in [0, T]$. Under the widely accepted linear system approximation, the data-model for the time signal writes as:

$$R_i(t)=\int_\Omega h(t-\tau(s,p_i))\chi(s)ds, \quad (4)$$

where $\chi(\cdot)$ is the unknown TRF. At the continuous limit (assuming infinitely many samples are available), it may be realized that the RF function can be successively expressed as:

$$RF(r) = \sum_{i=1}^{N} R_i[\tau(r, p_i)] \quad (5)$$

$$= \sum_{i=1}^{N} \int_0^T R_i(t)\delta(t-\tau(r, p_i))dt \quad (6)$$

$$= \sum_{i=1}^{N} \int_\Omega \int_0^T h(t-\tau(s, p_i))\delta(t-\tau(r, p_i))dt\chi(s)ds \quad (7)$$

$$= \sum_{i=1}^{N} \int_\Omega \int_0^T h(\tau(r, p_i)-\tau(s, p_i))\chi(s)ds \quad (8)$$

$$= \int_\Omega PSF(r, s)\chi(s)ds, \quad (9)$$

where use is made of the properties of the Dirac delta function $\delta(\cdot)$ and T is assumed to be large enough to ensure that $\tau(r, p_i) \in [0, T] \forall r \in \Omega \wedge \forall i \in [1, \ldots, N]$, and where the integration domain $\Omega$ corresponds to the 2D imaging plane. The PSF as eventually obtained corresponds to the PSF as defined in Eq. 2.

Now, it should be reminded that the above formula result from approximations and have limitations. First, the RF image cannot be directly computed as defined in Eq. 5, since only a finite number of time samples are available. Thus, an approximation is needed, as discussed earlier. For example, an interpolation scheme may be introduced to evaluate $R_i(t)$ at the desired delay, i.e., corresponding to an output of the time-of-flight function $\tau(r, p)$, evaluated for $p=p_i$. Yet, any computation of the PSF based on Eq. 1 or 2 may be performed using a same interpolation scheme. That is, a discrete version of the pulse h(t) can be interpolated using that same interpolation scheme, to cope with this practical limitation and avoid introduction of biases. Second, the derivation of Eqs. 4-9 relies on approximations: they are derived at the continuous limit, and under the assumption of the linear system approximation. In addition, the array pattern and attenuation were ignored, though they could easily be inserted, thanks to added correction factors $b_i$, as noted earlier.

As a further comment, note that if the function x(s) is substituted with a Dirac delta function in Eq. 9, i.e., $RF(r)=\int_\Omega PSF(r, s)\delta(s-r_0)\,cls$, the resulting RF function is equal to $RF(r)=PSF(r, r_0)$. Thus, the PSF function can be regarded as the RF image obtained for a single point reflector located in $r_0$. On this basis, a bivariate PSF function $PSF(r_1, r_2)$ is often depicted by fixing its second argument (here $r_2$), by convention. The resulting image can thus be displayed in the plane (x, y) in which $r_1$ is varied, as latter discussed in detail in reference to FIGS. 5-7.

As noted earlier, a spatially varying PSF is one for which $PSF(r_1, r_2)\neq PSF(r_1-(r_2-r_3), r_3)$, whereas, for a spatially invariant PSF, the condition $PSF_f(r_1, r_2)=PSF_f(r_1-(r_2-r_3), r_3)$ holds. Thus, saying that a PSF is spatially invariant means that the depiction of $PSF_f(r_1, r_3)$, where $r_3$ is fixed and $r_1$ is varied in the plane (x, y), yields a same image as $PSF_f(r_1, r_2)$, except that $PSF_f(r_1, r_3)$ is shifted so as to be centered on $r_3$ instead of $r_2$. On the contrary, $PSF(r_1, r_3)$ differs from $PSF(r_1, r_2)$ wherever $r_2 \neq r_3$.

The present methods may be applied to any ultrasound imaging technique, probe setup, or deconvolution methods. Accounting for the spatially varying behavior of the PSF dramatically impacts the accuracy of the reconstruction of the TRF, as illustrated in the next section. Yet, simple computational schemes are proposed herein, which leverage analytical formulations of the PSF. As a result, the TRF can be efficiently, yet accurately evaluated.

Figure 8:
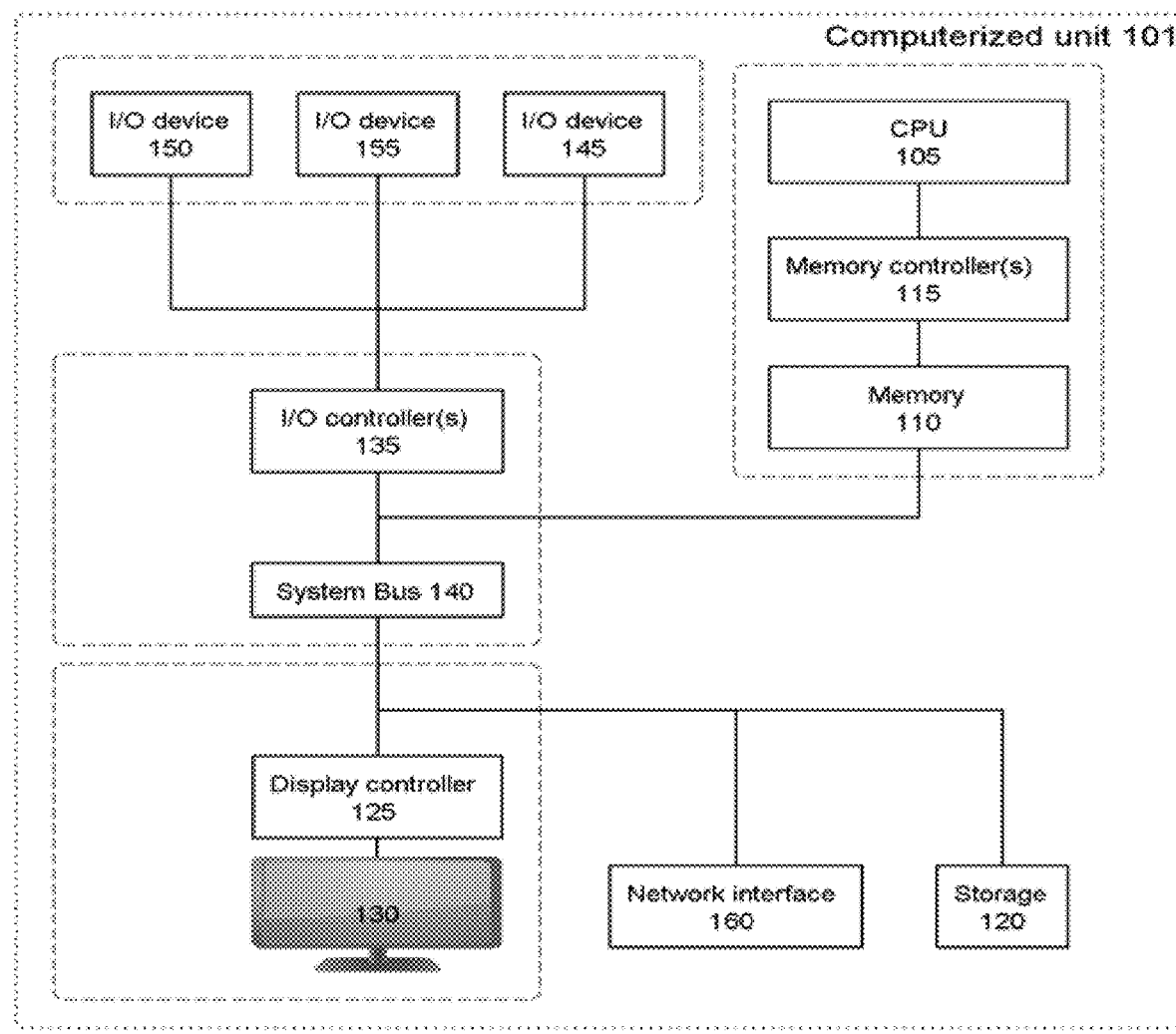
FIG. 8 schematically represents a general purpose computerized system, suited for implementing one or more method steps as involved in embodiments of the invention.

At present, referring more particularly to FIGS. 1, 2 and 8, another aspect of the invention is described, which concerns an ultrasound apparatus 1. The latter basically comprises an array 20 of transducers 21-28 (see FIG. 1) and a processing module 107 (see FIG. 2). The module 107 may be implemented in hardware or in software, the latter run, e.g., at a computerized unit 101 of a computerized device 10 connected to the array 20, so as to receive data from the transducers, as assumed in FIG. 1.

The transducers 21-28 may for instance be piezoelectric elements; they are each configured to convert an electrical signal into a sound wave, in order to emit S11 such a sound wave and, conversely, to convert a sound wave it receives S12 into an electrical signal. Thus, time signals can be obtained from the array of transducers, in operation.

For the sake of description, the processing module 107 can be regarded a set of distinct modules, the latter comprising a beamforming module 1071, a PSF computation module 1073, and a deconvolution module 1074.

The beamforming module 1071 is generally configured to beamform S13 time signals obtained S12 from the array of transducers. This way, RF data can be obtained S13, which data are assumed to correspond to outputs of a RF function, just as described earlier in reference to the present methods. That is, the RF function is again assumed to involve a convolution of the PSF function with the TRF and the PSF is assumed to be defined at pairs of points in the imaging plane, so as to account for a spatial variance thereof.

The PSF module 1073 is configured to compute the PSF, consistently with the methods disclosed herein. I.e., the module 1073 may access RF data as obtained via the beamforming module 1071 and compute S18-S22 the PSF, for each pair (r, s), as a sum of contributions from transducers 21-28, to which respective time-of-flight functions can be associated. As explained earlier, each contribution is computed by evaluating S20 the transfer function h, based on distinct outputs of a respective function $\tau$, evaluated at r and s.

Finally, the deconvolution module 1074 is configured to deconvolve the RF function associated to RF data as accessed by the PSF module 1073, so as to obtain the TRF and, this, based on a PSF as computed by the PSF module 1073, in operation.

Consistently with preferred embodiments of the present methods, the apparatus 1 may further comprise an interpolation module 1072. The latter shall typically be configured in the processing module 107 so as to be invoked by the beamforming module 1071. This way, the interpolation module 1072 may, upon request by the module 1071, interpolate time signals $R_i$ obtained from the transducers, so as to return corresponding interpolants to the beamforming module, for the latter to construct the RF function, in operation.

Preferably, the interpolation module 1072 is further configured in the processing module 107 so as to be invoked by the PSF module 1073 too. This way, the interpolation module 1072 may, upon request by the module 1073, interpolate the transfer function h, and return a corresponding interpolant to the PSF module 1073. More preferably, the transfer function h is interpolated based on a same interpolation scheme as used to interpolate the time signals, in order to obtain the RF function, as described earlier.

For completeness, and according to a final aspect, the invention can also be embodied as a computer program product for computing a tissue reflectivity function. This program may for instance be run on a computerized unit 101 of a device 10. This program shall typically implement functions of the module 107 depicted in FIG. 2. In all cases, the computer program product comprises a computer readable storage medium having program instructions embodied therewith, which program instructions are executable by a processing unit (e.g., such as unit 105 in FIG. 8), to cause the latter to take steps according to the present methods. Aspects of the present computer programs are discussed in detail in sect. 3.1 and 3.2.

The above embodiments have been succinctly described in reference to the accompanying drawings and may accommodate a number of variants. Several combinations of the above features may be contemplated. Examples are given in the next sections.

2. Specific Embodiments and Example of Applications

The specific embodiments described in this section assume the following inputs:

A given emitted-wave strategy, i.e., reflected by a time-of-flight law $\tau(r, p)$, which represents a wave's travel time from a position p of a given transducer on the array 20 to a point r on the imaging plane and back to p;

An array geometry expressed as transducer positions $p_1, \ldots, p_N$; and

A transducer's transfer function h(t), which determines the shape of the wave along the propagation direction.

An output of the PSF computation module 1073 (see sect. 1, FIG. 2) is then, for each pair (r, s) of points considered, an estimate of the PSF, e.g., computed according to Eq. 2. One assumes that Eq. 10 holds at the continuous limit (i.e., considering infinitely many time samples).

Any deconvolution method (e.g., formulated on a grid over the spatial domain Ω) may be contemplated for the computation of the PSF according to Eq. 2.

Figure 4A:
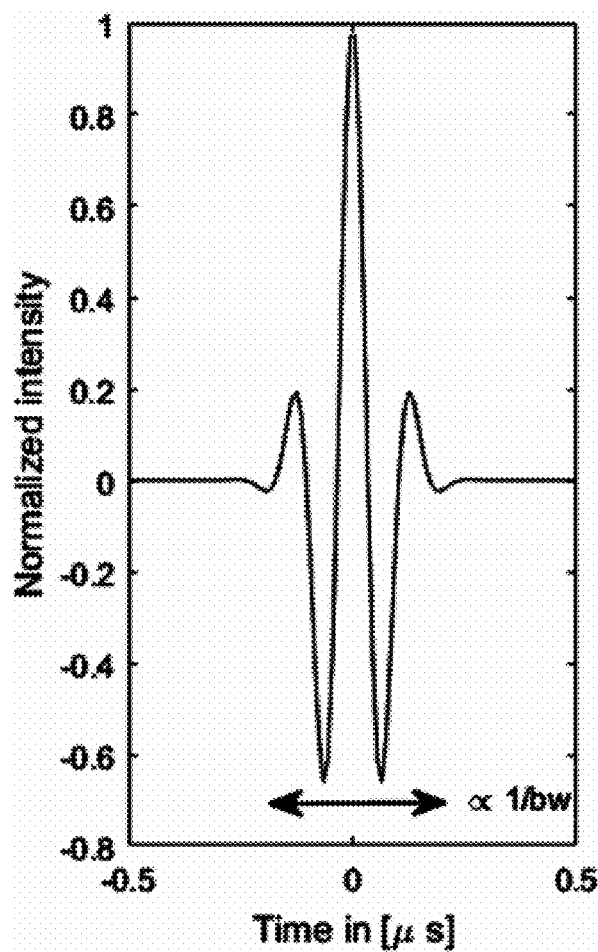
FIGS. 4A and 4B are plots representing a transfer function h as typically involved in embodiments.
Figure 4B:
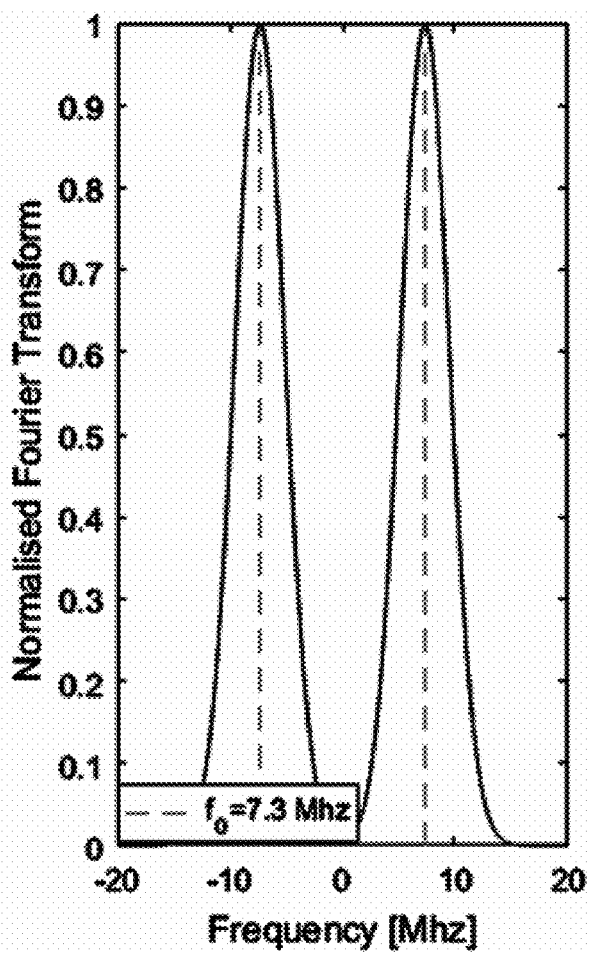

The following assumes a linear array of transducers, arranged along the x-direction, located at y=0. The transfer function h is further assumed to follow a Gaussian pulse model, i.e., $$h(t) = e^{\alpha t^2} \cos(2\pi f_0 t),$$

where α is a function increasing with the transducer bandwidth (BW), and $f_0$ denotes a central operating frequency of this transducer, see FIGS. 4A and 4B. The graphs depicted in FIGS. 4A and 4B assume a frequency $f_0$=10 MHz and a bandwidth BW=0.8$f_0$. The resulting transfer function is depicted in the time domain in FIG. 4A and in the frequency domain in FIG. 4B.

2.1 Plane Wave Configuration

For emission, assuming that electrical excitation signals are simultaneous created across the array 20, a plane wave results by coherent summation of circular waves emitted by each transducer. The planar wave front may be scattered back to the array with a circular wave, when encountering a particular point, interface, inhomogeneity, etc., of the target medium 30. Assuming the plane wave is directed in the y-direction, the time-of-flight is then given by:

$$\tau(r, p_i) = (r, e_y)/c + \|r - p_i\|/c,$$

where c the speed of sound in the target medium 30.

Figure 5B:
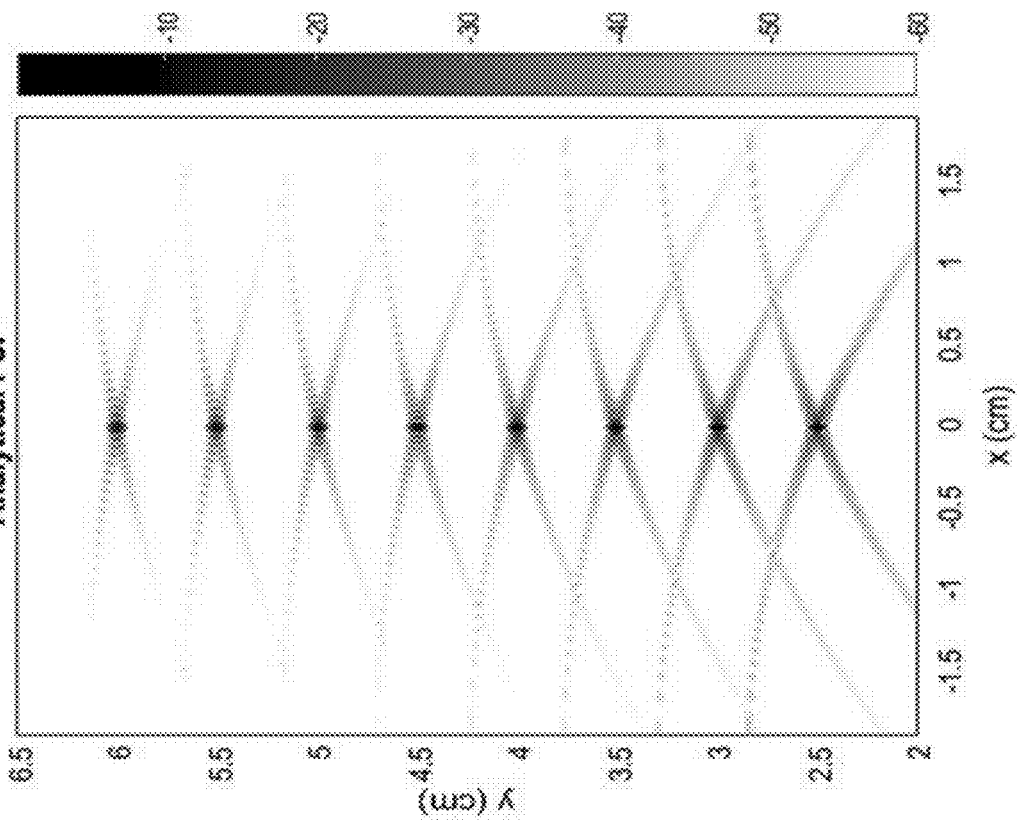
FIGS. 5A and 5B are graphs representing point spread functions pertaining to a linear array of 128 transducers configured to generate a plane wave, as respectively obtained according to: (i) known simulation methods (not according to this invention, FIG. 5A); and (ii) embodiments of this invention (FIG. 5B).

Contrary to the naïve depiction of FIG. 1, a typical transducer array may involve numerous transducers, e.g., 64 or 128 transducers, as assumed in this section. For instance, FIG. 5B depicts an "analytical" PSF as computed according to Eq. 2, for a plane wave and assuming a linear array of 128 transducers, with $f_0$=5 Mhz and BW=0.4 $f_0$.

Figure 5A:
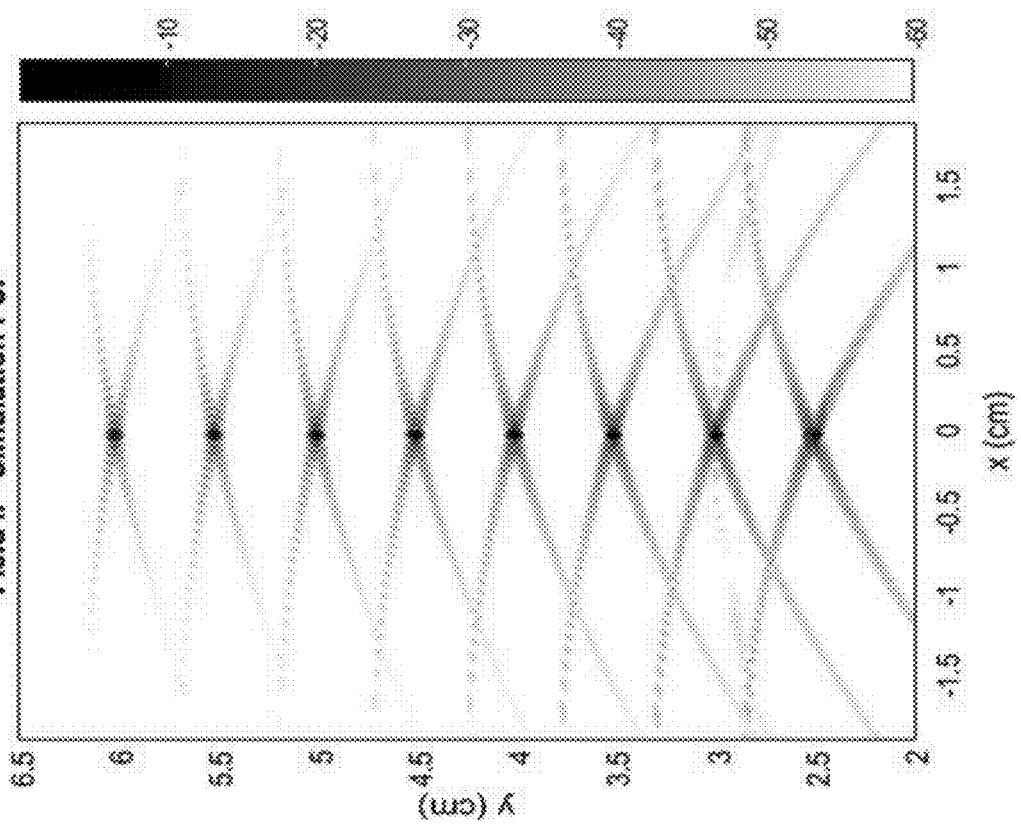

Note that, as per the convention evoked in sect. 1, each of these PSFs is displayed by fixing its second argument $r_2$ and varying its first argument $r_1$ in the plane (x, y). Now, what is actually displayed in FIGS. 5 and 6 is a sum of PSFs, as obtained for a collection of M fixed points, the sum being performed over each of these fixed points. That is, the function depicted, call it $\Sigma(r_1)$, is defined by: $\Sigma(r_1) = \Sigma_{k=1}^{M} PSF(r_1, r_k)$. In FIGS. 5A and 5B, the points $r_k$ are uniformly distributed along the axis y (for x=0) and each contribution to $\Sigma(r_1)$ gives rise to a respective pattern formed by a dark spot, surrounded by a pattern of lighter spots. Comparing FIGS. 5A and 5B, we observe a great similarity between the present PSF and the PSF as simulated with the software Field II. In particular, the present approach captures well the spatially varying nature of the PSF implied by the delay law and probe geometry.

2.2 Divergent Wave

It is now assumed that electrical excitation signals are delayed in order to form a coherent divergent wave, having a virtual point source $r_n = (x_n, y_n)$. The diverging front wave is scattered back with circular waves when encountering, e.g., inhomogeneities in the medium, whereby the time-of-flight is now given by $\tau(r, p_i) = (\|r - r_n\| - (r_n, r)/c + \|r - p_i\|/c$.

Figure 6B:
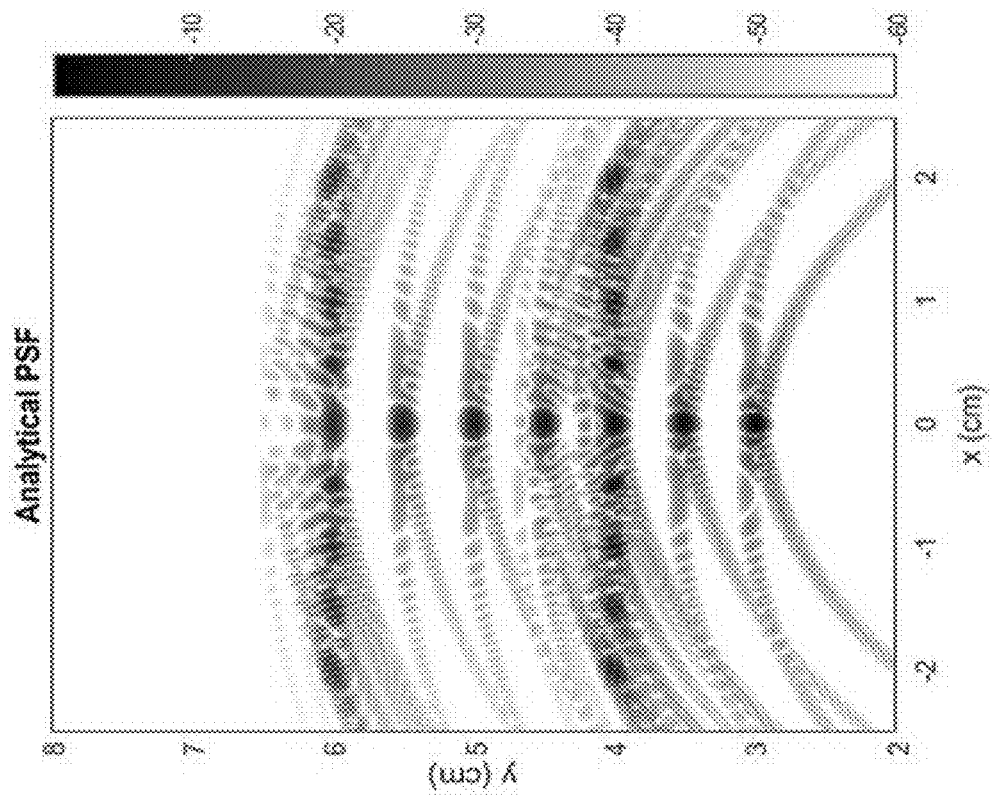
FIGS. 6A and 6B are graphs representing point spread functions corresponding to a linear array of 64 transducers, configured to generate a divergent wave.
Figure 6A:
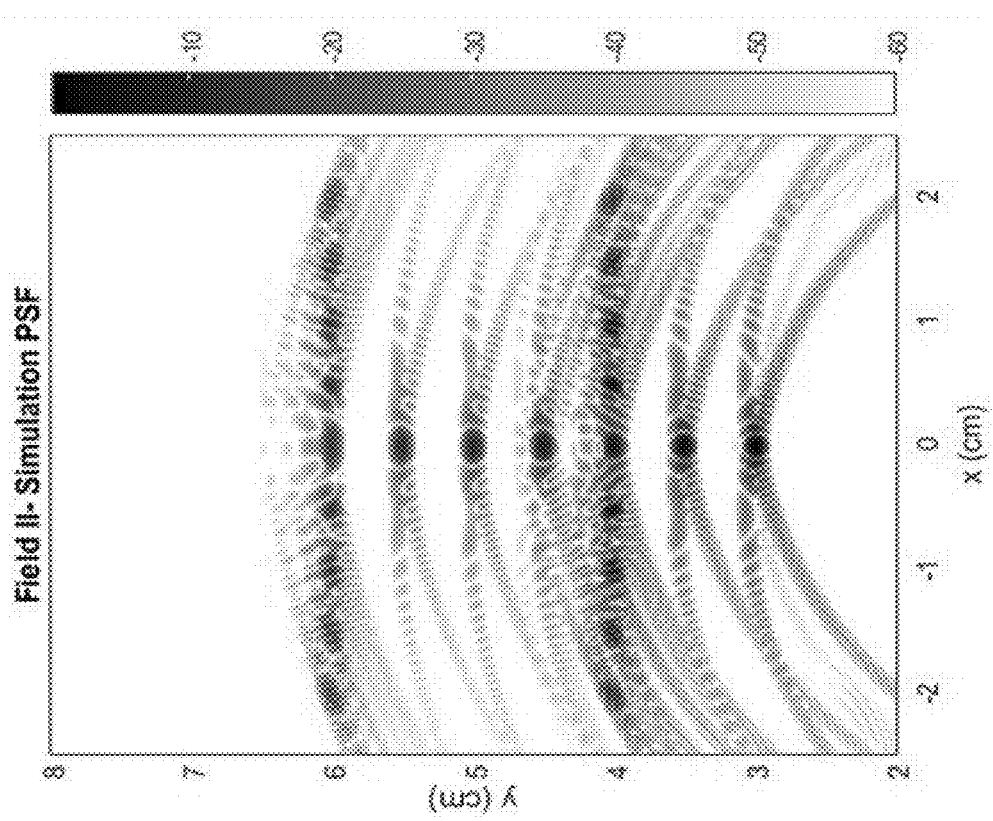

FIG. 6B depicts the PSF as computed according to Eq. 2, for a divergent wave, and assuming a linear array of 64 transducers, with $f_0$=2.5 Mhz and BW=0.4 $f_0$. Again, what is actually displayed in FIGS. 6A and 6B is a sum of PSFs obtained for a collection of fixed points. However, this time, the points $r_k$ are uniformly distributed on a grid, which is identical to that depicted in FIG. 7C. The obtained patterns are, accordingly, somewhat more involved. In particular, the PSFs now strongly vary over the imaging plane and, in particular, exhibit a rotated pattern far from the center. Yet, the PSF as computed according to embodiments (FIG. 6B) compares again favorably with that of FIG. 6A, simulated with Field II.

2.3 Impact on Sparse Deconvolution

As seen in FIGS. 6A, 6B, a spatially invariant approximation of the PSF may be markedly insufficient in some cases and may thus have severe consequences on the subsequent deconvolution. The present subsection illustrates the weakness of such an approximation, when using an $l_1$ deconvolution algorithm.

Figure 7B:
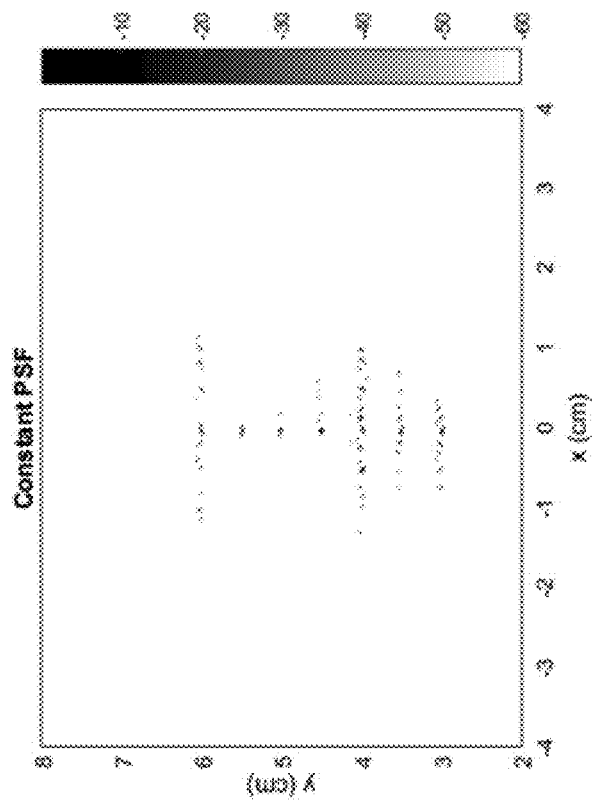
FIGS. 7A and 7B depict deconvolution results as respectively obtained with: (i) a spatially varying point spread function computed according to an embodiment (FIG. 7A); and (ii) a spatially invariant point spread function (FIG. 7B, not according to the invention).
Figure 7A:
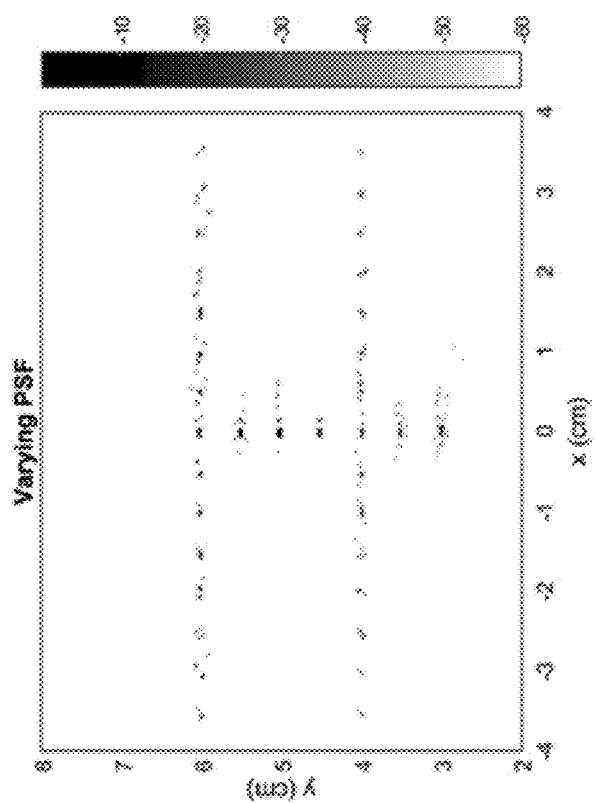
Figure 7D:
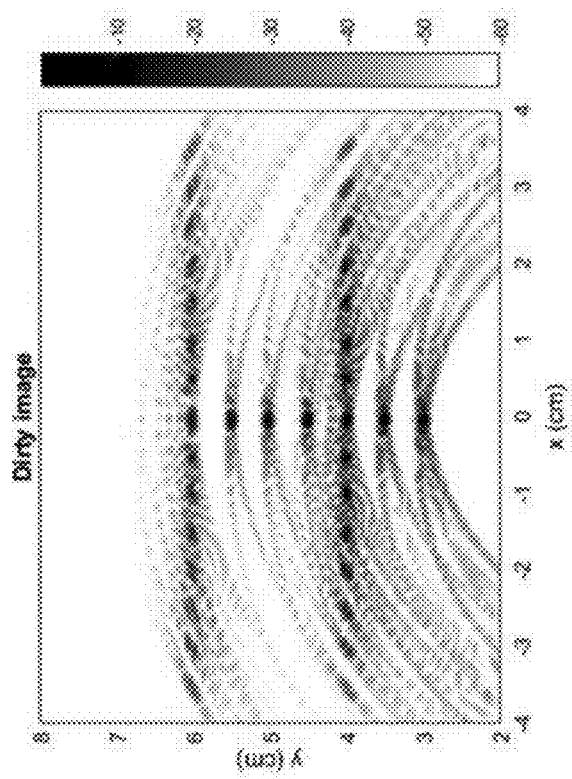
FIG. 7D shows a corresponding radio frequency (RF) image as obtained by a mere delay-and-sum method. The graphs of FIGS. 7A-7D otherwise assume a same setup as in FIGS. 6A and 6B.
Figure 7C:
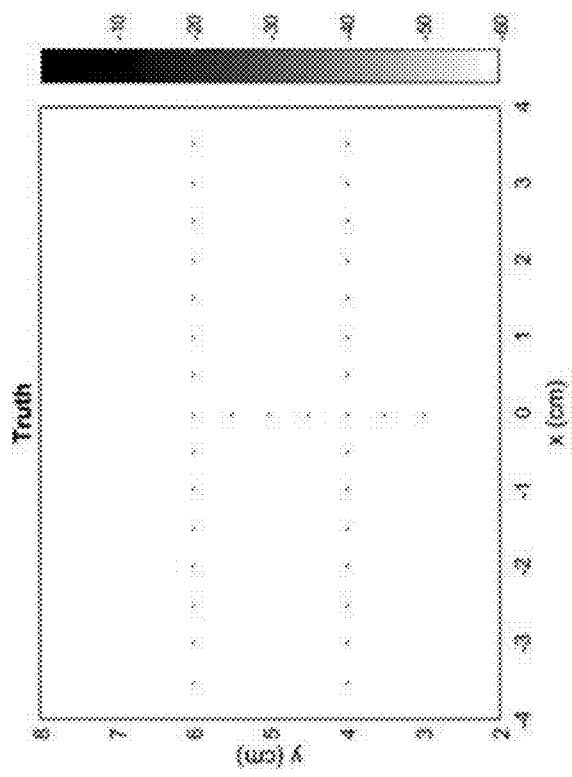
FIG. 7C is an image of a test medium, consisting of point reflectors only

Deconvolution results are shown in FIGS. 7A, 7B, which both depict TRFs as estimated by deconvoluting a RF function (FIG. 7D), which was obtained from the test medium of FIG. 7C (i.e., consisting of point reflectors only), using a mere DAS technique. Data were generated using Field II, assuming a divergent wave on the same setup as in FIGS. 6A, 6B. FIG. 7A show deconvolution results, using a spatially varying PSF, computed according to embodiments (and based on Eq. 2), whereas FIG. 7B was obtained using a spatially invariant PSF. In both cases, an $l_1$ promoting regularization was relied on.

As seen in FIGS. 7A-7D, a deconvolution that assumes a spatially invariant PSF allows an acceptable recovery of the point scatters only near the center, where the approximation remains acceptable. However further apart from point (0, 5) cm, a reasonable recovery is only possible when the spatial variation of the PSF is taken into account.

3. Technical Implementation Details 3.1 Computerized Systems and Devices

Computerized systems and devices can be suitably designed for implementing embodiments of the present invention as described herein. In that respect, it can be appreciated that the methods described herein are largely non-interactive and automated. In exemplary embodiments, the methods described herein can be implemented either in an interactive, partly-interactive or non-interactive system. The methods described herein can be implemented in software, hardware, or a combination thereof. In exemplary embodiments, the methods described herein are implemented in software, as an executable program, the latter executed by suitable digital processing devices. More generally, embodiments of the present invention can be implemented wherein general-purpose digital computers, such as personal computers, workstations, etc., are used.

For instance, the system depicted in FIG. 8 schematically represents a computerized unit 101, e.g., a general- or specific-purpose computer, which may be used in place or as part of the computerized device 10 of FIG. 1. As such, the unit 101 may interact with the array 20 of transducers 21-28, e.g., via suitable converters and I/O units 145-155.

In exemplary embodiments, in terms of hardware architecture, as shown in FIG. 8, the unit 101 includes a processor 105, and a memory 110 coupled to a memory controller 115. One or more input and/or output (I/O) devices 145, 150, 155 (or peripherals) are communicatively coupled via a local input/output controller 135. The input/output controller 135 can be coupled to or include one or more buses and a system bus 140, as known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 105 is a hardware device for executing software, particularly that stored in memory 110. The processor 105 can be any custom made or commercially available processor, a central processing unit (CPU), an auxiliary processor among several processors associated with the computer 101, a semiconductor based microprocessor (in the form of a microchip or chip set), or generally any device for executing software instructions.

The memory 110 can include any one or combination of volatile memory elements (e.g., random access memory) and nonvolatile memory elements. Moreover, the memory 110 may incorporate electronic, magnetic, optical, and/or other types of storage media. Note that the memory 110 can have a distributed architecture, where various components are situated remote from one another, but can be accessed by the processor 105.

The software in memory 110 may include one or more separate programs, each of which comprises an ordered listing of executable instructions for implementing logical functions. In the example of FIG. 8, the software in the memory 110 includes methods described herein in accordance with exemplary embodiments and, in particular, a suitable operating system (OS) 111. The OS 111 essentially controls the execution of other computer programs and provides scheduling, input-output control, file and data management, memory management, and communication control and related services.

The methods described herein may be in the form of a source program, executable program (object code), script, or any other entity comprising a set of instructions to be performed. When in a source program form, then the program needs to be translated via a compiler, assembler, interpreter, or the like, as known per se, which may or may not be included within the memory 110, so as to operate properly in connection with the OS 111. Furthermore, the methods can be written as an object oriented programming language, which has classes of data and methods, or a procedure programming language, which has routines, subroutines, and/or functions.

Possibly, a conventional keyboard and mouse can be coupled to the input/output controller 135. Other I/O devices 140-155 may include or be connected to other hardware devices 10, as noted earlier.

In addition, the I/O devices 140-155 may further include or be connected to devices 410, 510, 610 that communicate outputs, e.g., time series. The computerized unit 101 can further include a display controller 125 coupled to a display 130. In exemplary embodiments, the computerized unit 101 can further include a network interface or transceiver 160 for coupling to a network, to enable, in turn, data communication to/from other, external components.

The network transmits and receives data between the unit 101 and external devices, e.g., transducers 21-28. The network is possibly implemented in a wireless fashion, e.g., using wireless protocols and technologies, such as Wifi, WiMax, etc. The network may be a fixed wireless network, a wireless local area network (LAN), a wireless wide area network (WAN) a personal area network (PAN), a virtual private network (VPN), intranet or other suitable network system and includes equipment for receiving and transmitting signals.

The network can also be an IP-based network for communication between the unit 101 and any external server, client and the like via a broadband connection. In exemplary embodiments, network can be a managed IP network administered by a service provider. Besides, the network can be a packet-switched network such as a LAN, WAN, Internet network, an Internet of things network, etc.

If the unit 101 is a PC, workstation, intelligent device or the like, the software in the memory 110 may further include a basic input output system (BIOS). The BIOS is stored in ROM so that the BIOS can be executed when the computer 101 is activated. When the unit 101 is in operation, the processor 105 is configured to execute software stored within the memory 110, to communicate data to and from the memory 110, and to generally control operations of the computer 101 pursuant to the software.

The methods described herein and the OS 111, in whole or in part are read by the processor 105, typically buffered within the processor 105, and then executed. When the methods described herein are implemented in software, the methods can be stored on any computer readable medium, such as storage 120, for use by or in connection with any computer related system or method.

3.2 Computer Program Products

The present invention may be an apparatus, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the C programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, any suitable number of transducers may be contemplated, other than N=8, 64 or 128 as assumed in examples described herein.

What is claimed is:

1. A computer-implemented method for computing a tissue reflectivity function (TRF), comprising:

accessing radio-frequency (RF) data obtained by beamforming time signals R from an array of transducers of an ultrasound device, wherein the RF data correspond to outputs of a radio-frequency (RF) function evaluated at given points r of an imaging plane, wherein the RF function involves a convolution of a point spread function (PSF) with the TRF to be computed, wherein the array of transducers is configured to cause, in emission, a coherent divergent wave having a virtual point source $r_n = (x_n, y_n)$, wherein the virtual point source is located behind the array of transducers; and computing a time-of-flight function τ associated with an $i^{th}$ transducer of the array for the given point r, as $\tau(r, p_i) = (\|r-r_n\| - (r_n, r)/c + \|r-p_i\|)/c$, wherein:

c is the speed of sound in a given target medium, whose TRF is to be computed; and $p_i$ corresponds to a position of said $i^{th}$ transducer;

defining, without a simulation, the PSF at pairs of the given points in the imaging plane to account for a spatial variance of the imaging plane;

for each pair of the given pairs of points in the imaging plane, computing the PSF as a sum of contributions from at least two of the transducers to which respective time-of-flight functions are associated;

computing each of the contributions to the PSF by evaluating a transducer's transfer function h, based on two outputs of a respective time-of-flight function τ, said two outputs obtained by evaluating the time-of-flight function at a first point r and at a second point s of said each pair, respectively;

deconvoluting the RF function based on the computed PSF to obtain the TRF; and displaying an image based on the obtained TRF.

2. The method according to claim 1, wherein at computing the PSF, each of said contributions is computed by evaluating the transducer's transfer function h as a function of a difference between said two outputs.

3. The method according to claim 2, wherein the PSF is computed as a sum that is written as $\Sigma_i h(\tau(r, p_i) - \tau(s, p_i)) \times b_i$, where $p_i$ denotes a position in space of an $i^{th}$ transducer of the array, i=1, ... N, and $b_i$ is a correction factor.

4. The method according to claim 3, wherein at computing the PSF, each $b_i$ is equal to 1.

5. The method according to claim 1, wherein the method further comprises:

accessing an explicit representation of the RF function that is constructed based on time signals $R_i$ obtained from the transducers of said array, and wherein the TRF is subsequently obtained by deconvoluting the constructed RF function, based on the accessed representation of the RF function.

6. The method according to claim 5, wherein the RF function is constructed by interpolating the time signals $R_i$ obtained from the transducers to obtain said explicit representation of the RF function.

7. The method according to claim 6, wherein computing the PSF further comprises:

interpolating the transfer function h, based on a same interpolation scheme as used to interpolate the time signals $R_i$ to construct the RF function.

8. The method according to claim 1, wherein the method further comprises:

accessing a representation of the transducer's transfer function h as an analytical function, prior to evaluating the transducer's transfer function.

9. The method according to claim 8, wherein the analytical function accessed is a decaying function times an oscillating function.

10. The method according to claim 9, wherein the analytical function h accessed is written as $h(t) = \beta e^{-\alpha t^2} \cos(2\pi f_0 t)$, where β is a constant.

11. A computer program product for computing a tissue reflectivity function (TRF) the computer program product comprising a computer readable storage medium having program instructions embodied therewith, the program instructions being executable by a processing unit to cause the latter to:

accessing radio-frequency (RF) data obtained by beamforming time signals R from an array of transducers of an ultrasound device, wherein the RF data correspond to outputs of a radio-frequency (RF) function evaluated at given points r of an imaging plane, wherein the RF function involves a convolution of a point spread function (PSF) with the TRF to be computed, wherein the array of transducers is configured to cause, in emission, a coherent divergent wave having a virtual point source $r_n = (x_n, y_n)$, wherein the virtual point source is located behind the array of transducers; and computing a time-of-flight function τ associated with an $i^{th}$ transducer of the array, for the given point r, as $\tau(r, p_i) = (\|r-r_n\| - (r_n, r)/c + \|r-p_i\|)/c$, wherein:

c is the speed of sound in a given target medium, whose TRF is to be computed; and $p_i$ corresponds to a position of said $i^{th}$ transducer;

defining, without a simulation, the PSF at pairs of the given points in the imaging plane to account for a spatial variance of the imaging plane;

for each pair of the given pairs of points in the imaging plane, computing the PSF as a sum of contributions from at least two of the transducers to which respective time-of-flight functions are associated;

computing each of the contributions to the PSF by evaluating a transducer's transfer function h, based on two outputs of a respective time-of-flight function τ, said two outputs obtained by evaluating the time-of-flight function at a first point r and at a second point s of said each pair, respectively;

deconvoluting the RF function based on the computed PSF to obtain the TRF; and displaying an image based on the obtained TRF.

12. The computer program product according to claim 11, wherein at computing the PSF, each of said contributions is computed by evaluating the transducer's transfer function h as a function of a difference between said two outputs.

13. The computer program product according to claim 12, wherein the PSF is computed as a sum that is written as $\Sigma_i h(\tau(r, p_i) - \tau(s, p_i)) \times b_i$, where $p_i$ denotes a position in space of an $i^{th}$ transducer of the array, i=1, ... N, and $b_i$ is a correction factor.

14. The computer program product according to claim 13, wherein:

at computing the PSF, each $b_i$ is equal to 1.

* * * * *